United States Patent
Kim et al.

(10) Patent No.: US 8,702,593 B2
(45) Date of Patent: Apr. 22, 2014

(54) CAPSULE ENDOSCOPE

(75) Inventors: Sungwan Kim, Seoul (KR); Youdan Kim, Seoul (KR); Chiwon Lee, Gyeonggi-do (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 13/546,949

(22) Filed: Jul. 11, 2012

(65) Prior Publication Data

US 2013/0018224 A1    Jan. 17, 2013

(30) Foreign Application Priority Data

Jul. 15, 2011 (KR) .................. 10-2011-0070613

(51) Int. Cl.
*A61B 1/00* (2006.01)
*A61B 1/06* (2006.01)

(52) U.S. Cl.
USPC ........... 600/118; 600/103; 600/117; 600/160; 600/178

(58) Field of Classification Search
USPC .................. 600/103, 117, 118, 160, 178
See application file for complete search history.

(56) References Cited

U.S. PATENT DOCUMENTS

| | | | | |
|---|---|---|---|---|
| 5,906,476 A | * | 5/1999 | Arlton .................. | 416/114 |
| 6,240,312 B1 | * | 5/2001 | Alfano et al. .......... | 600/476 |
| 7,711,413 B2 | | 5/2010 | Feldman et al. | |
| 2003/0214579 A1 | * | 11/2003 | Iddan .................. | 348/81 |
| 2005/0036059 A1 | * | 2/2005 | Goldwasser ........... | 348/373 |
| 2006/0004276 A1 | * | 1/2006 | Iddan et al. ........... | 600/407 |
| 2007/0200027 A1 | * | 8/2007 | Johnson ................ | 244/3.1 |
| 2011/0098534 A1 | * | 4/2011 | Segawa et al. ......... | 600/118 |

FOREIGN PATENT DOCUMENTS

| | | |
|---|---|---|
| KR | 1020060030019 | 4/2006 |
| KR | 1020100107638 | 10/2010 |

* cited by examiner

*Primary Examiner* — Philip R Smith
*Assistant Examiner* — Rynae Boler
(74) *Attorney, Agent, or Firm* — Wells, St. John P.S.

(57) ABSTRACT

Disclosed herein is a maneuverable capsule endoscope. A capsule body is input into an internal organ to take images of the inside of the internal organ. A fan unit is mounted on the body. A fan position-changing device changes a direction in which the fan unit discharges fluid. The fan unit is mounted inside a duct without damaging the inner wall of the internal organ. When input into the internal organ, the capsule endoscope can concentrically take images of a specific portion inside the internal organ, and can freely take images of a portion that is intended to be photographed.

20 Claims, 9 Drawing Sheets

CAPSULE ENDOSCOPE

CROSS REFERENCE TO RELATED APPLICATION(S)

This application claims the benefit of Korean Patent Application No. 10-2011-0070613, filed Jul. 15, 2011, which is hereby incorporated by reference in its entirety into this application.

BACKGROUND OF THE INVENTION

1. Technical Field

The present invention relates generally to a capsule endoscope and, more particularly, to a capsule endoscope that is configured such that the inside of internal organs can be more easily photographed.

2. Description of the Related Art

In general, endoscopes have a camera and an illumination lamp mounted on one end of a flexible hose. When the endoscope is inserted into a body, the illumination lamp emits light and the camera photographs an internal organ of the body and transmits photographed images to a monitor, so that the internal organ can be checked.

Endoscopes have undergone extensive development and are widely used in the medical field in response to the development of fiber optics and the development of micro camera technologies.

Endoscopes cause pain and an unpleasant feeling in patients when they undergo an examination because the flexible hose must be inserted into the internal organ as described above via the gullet or the anus, and thus are not welcomed by patients.

In an example, in the case of a colon endoscope, the pain that a patient suffers and the accuracy of judgment about a lesion are greatly be determined the experience and skillfulness of a doctor.

In order to overcome such problems with endoscopes, a capsule endoscope that a patient can swallow was recently developed.

The capsule endoscope has a wireless camera system mounted on the capsule. Information about images of an internal organ of a human body taken by the wireless camera system is transmitted to the outside so that the inside of the internal organ of a person can be examined.

However, the capsule endoscope is configured such that it passively moves due to vermiculation of internal organs of a human body after being input into the organs through the gullet. Therefore, the problem is that images can be taken only when the capsule endoscope is naturally digested in the digestive system.

In addition, there is a problem in that the capsule endoscope cannot concentrically photograph an object that is the target of observation, in particular, a specific digestive system. Furthermore, it is impossible to observe a region that requires re-observation by moving the capsule endoscope back to that same region.

Moreover, there is a problem in that the capsule endoscope requires fasting state.

SUMMARY OF THE INVENTION

Accordingly, the present invention has been made keeping in mind the above problems occurring in the prior art, and an object of the present invention is to provide a capsule endoscope that, when input into the internal organ, can concentrically take images of a specific portion while staying in a specific region inside an internal organ without the movable device damaging the internal organ and which can freely move to a position in which re-observation is required, so that an accurate diagnosis can be made.

In order to accomplish the above object, the present invention provides a capsule endoscope that includes a capsule body, the capsule body comprising a camera capable of taking an image of an inside of an internal organ and a wireless transceiver, which communicates with an outside in order to control a movement of the capsule endoscope; a fan unit, which is mounted on the capsule body and is rotated by a motor, thereby discharging a fluid out of the capsule body; and a fan position-changing device, which changes a direction in which the fan unit discharges the fluid.

According to an embodiment of the invention, the fan unit may include a first fan unit, which is mounted on the capsule body, and discharges the fluid out of the capsule body; and a second fan unit, which is mounted opposite the first fan unit in the capsule body, and discharges the fluid in a direction different from that of the first fan unit.

According to an embodiment of the invention, the fan unit may include a fan, which is rotated by the motor, and a duct, in which the fan is disposed. The duct has a fluid inlet through which the fluid is introduced into the duct when the fan operates. The capsule body has a fluid inflow space formed therein, wherein the fluid inflow space is divided by a partition plate, and the fluid to be discharged by the fan unit is introduced into the fluid inflow space. The first fan unit, the second fan unit and the fan position-changing device are mounted inside the fluid inflow space of the capsule body, wherein the first fan unit and the second fan unit are disposed in a vertical direction of the capsule body facing oppositely in order to discharge the fluid upward and downward with respect to the capsule body.

According to an embodiment of the invention, the capsule endoscope may further include a fluid passage duct member disposed in the fluid inflow space, wherein the fan unit and the fan position-changing device are mounted inside the fluid passage duct member, and wherein the fluid passage duct member has a duct inlet through which the fluid is introduced.

According to an embodiment of the invention, the fan position-changing device may include a fan-fixing section to which the fan unit is fixed; a fan support to which the fan-fixing section is connected such that an angle thereof is freely adjustable; and a plurality of angle adjustment sections, which are disposed below the fan-fixing section and are spaced apart from each other, the angle adjustment sections changing an angle of the fan-fixing section.

According to an embodiment of the invention, the fan-fixing section and the fan support are connected to each other by a ball connector.

According to an embodiment of the invention, each of the angle adjustment sections may include a first movable member, which is provided on the fan support such that the first movable member is movable upward and downward; a connecting link member, which is connected to the first movable member and the fan-fixing section; and an actuator, which operates to linearly move the first movable member.

According to an embodiment of the invention, both ends of the connecting link member may be connected to the first movable member and to the fan-fixing section by ball connectors, respectively.

According to an embodiment of the invention, each of the angle adjustment sections may include an actuation link member, which is connected to the fan-fixing section and the fan support and which has an adjustable length; and a link-moving section, which adjusts the length of the actuation link member.

According to an embodiment of the invention, both ends of the actuation link member are connected to the fan-fixing section and the fan support by ball connectors, respectively.

According to an embodiment of the invention, the actuation link member may include a fixing link, which is connected to one of the fan-fixing section and the fan support; and a movable link, which is movably coupled to the fixing link, and is connected to the other one of the fan-fixing section and the fan support.

According to an embodiment of the invention, the link-moving section may include a movable screw, which is disposed in a longitudinal direction of the fixing link, and to which the movable link is screw-coupled; and a motor, which rotates the movable screw.

According to an embodiment of the invention, the movable link may be movably connected to an inside of the fixing link. A movement guide protrusion may extend from an outer circumference of the movable link, the movement guide protrusion being held inside the fixing link in order to prevent the movable link from rotating along with the screw when the screw rotates.

According to an embodiment of the invention, the angle adjustment sections, which are disposed below the fan-fixing section, at intervals of 90° about a central portion of the fan unit.

According to an embodiment of the invention, the fan unit may include a fan, which is rotated by the motor; and a duct inside which the fan is disposed. The fan position-changing device may include a fan-rotating section, which is provided in the duct, and changes the direction in which the fan discharges the fluid by rotating the fan; and a duct-rotating section, which is connected to the duct, and rotates the duct in a direction different from a direction in which the fan rotates.

According to an embodiment of the invention, the fan-rotating section may include a first motor, which is mounted on the duct, and generates rotational force; and a first rotary shaft, which rotates by receiving the rotational force from the first motor, and is connected to the fan such that the fan rotates. The duct-rotating section may include a second motor, which is mounted in the capsule body, and generates rotational force; and a second rotary shaft, which rotates by receiving the rotational force from the second motor, and is connected to the duct such that the duct rotates.

According to an embodiment of the invention, the first rotary shaft and the second rotary shaft may be disposed such that the first and second rotary shafts are perpendicular to each other on a plane.

The capsule endoscope of the invention can concentrically take photographs of one region inside an internal organ when input into the internal organ, and correctly take photographs of a region that requires observation while moving freely.

The present invention has the effects of improving the accuracy of an endoscopic examination, rendering accurate diagnosis possible, and preventing erroneous diagnosis.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
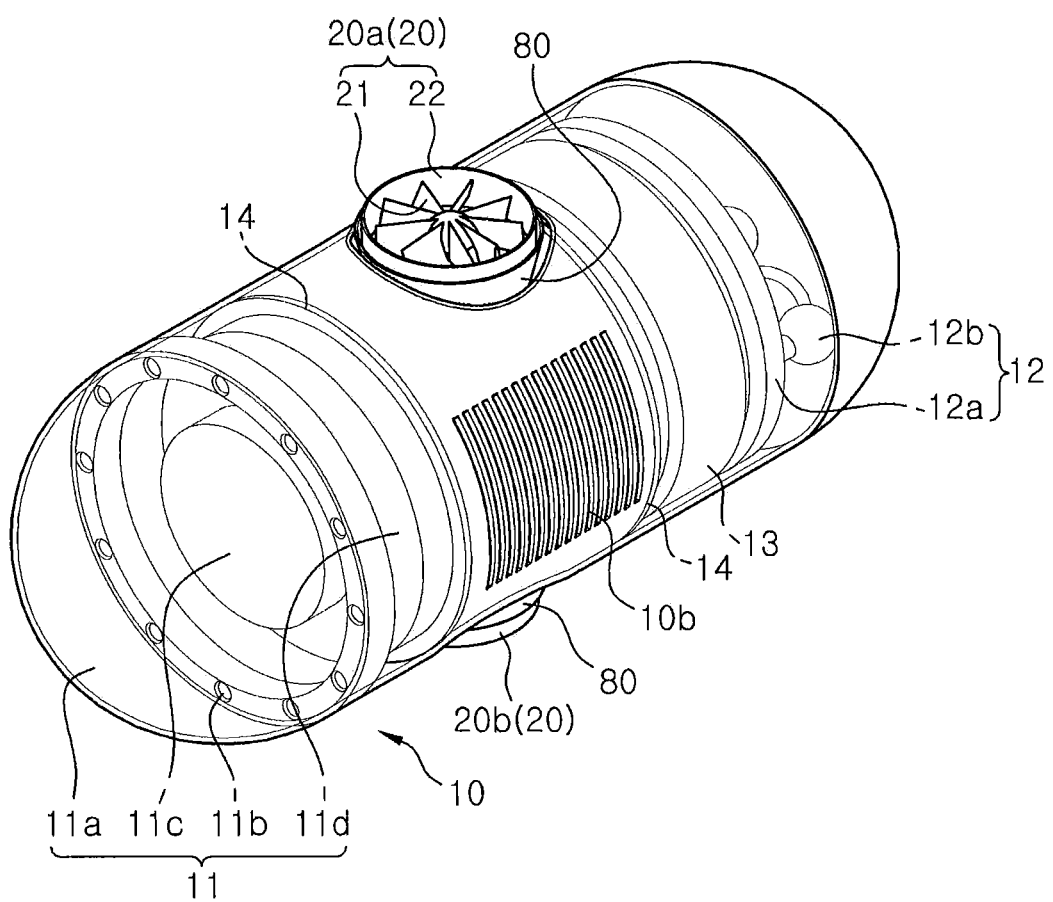
FIG. 1 is a perspective view showing a capsule endoscope according to the invention.

Reference now should be made to the drawings, in which the same reference numerals are used throughout the different drawings to designate the same or similar components.

Figure 3:
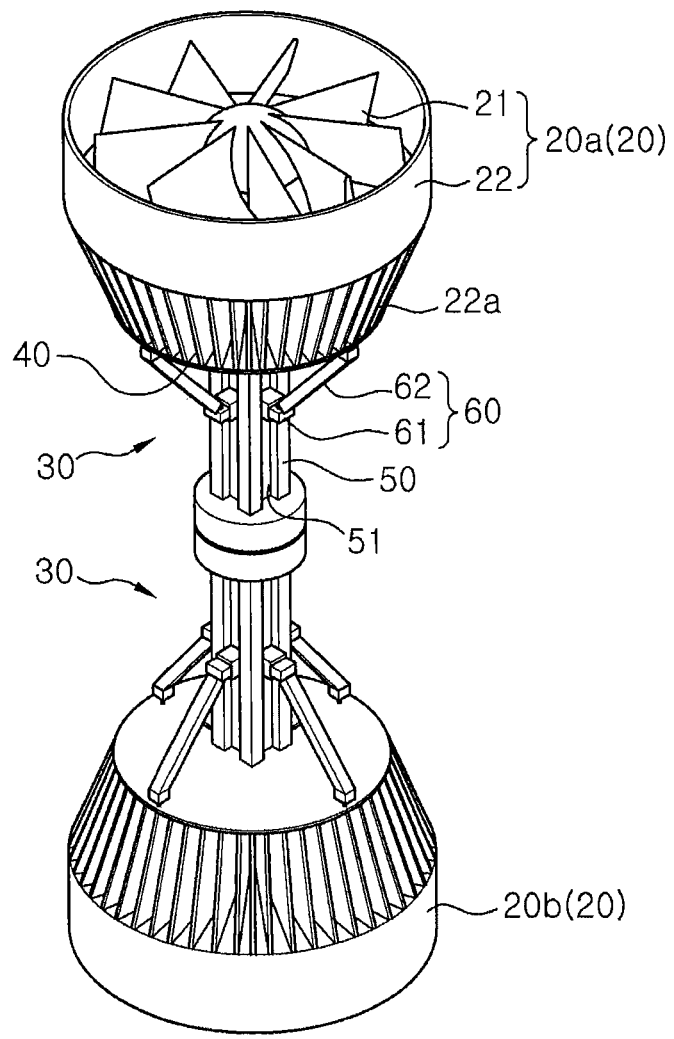
FIG. 3 is a perspective view showing fan position-changing devices according to the invention.

Referring to FIG. 1 and FIG. 3, a capsule endoscope according to an embodiment of the invention includes a capsule body 10, which is input into an internal organ of a human body through the gullet. The capsule body 10 has the shape of a capsule which has hemispherical caps on both ends and a fan, which is protected by a duct such that it moves safely without damaging the inner wall of the internal organ.

A camera 11, which can photograph the inside of the internal organ, and a wireless transceiver circuit, which can transmit an image photographed by the camera 11 to the outside and which can freely control the movement of the capsule endoscope, are provided inside the capsule body 10.

The camera 11 includes an optical dome 11a, which is provided on one end of the capsule body 10, a light source 11b, which is provided inside the capsule body 10, in the portion in which the optical dome 11a is disposed, such that it emits light through one portion of the capsule body 10, a lens 11c, which is provided in the optical dome 11a inside the capsule body 10, and an image detector 11d.

In addition, a wireless transceiver 12, which transmits the image photographed by the camera 11 to the outside, is provided inside the capsule body 10. The wireless transceiver 12 includes a transceiver body 12a and an antenna 12b, and not only transmits the image taken by the camera 11 to the outside but also transmits/receives an operation control signal of a fan motor (not shown), which will be described later, and fan position-changing devices 30.

In addition, a battery 13, which supplies power necessary for operating the camera 11, the wireless transceiver 12, the motor (not shown), which will be described later, is provided inside the capsule body 10.

In addition, fan units 20, which are rotated by the fan motor (not shown), are provided in the capsule body 10. The fan units 20 can eject fluid out of the capsule body 10 so that the position of the capsule body 10 can be changed and adjusted using the force of the ejected fluid.

Each of the fan units 20 includes a fan 21, which is rotated by the fan motor, and a duct 22. The fan 21 is disposed inside the duct 22. In the fan unit 20, the fan 21 is disposed inside the duct 22 but does not protrude outside the duct 22.

The fan unit 20 is configured such that the fan 21 does not contact the internal organ while operating, so that the fan unit 20 can safely operate inside the internal organ.

The duct 22 has a fluid inlet 22a through which the fluid is introduced into the duct 22 when the fan 21 operates. In an example, a plurality of the fluid inlets 22a is provided in the outer surface of a part that is opposite an outlet located around the fan 21 mounted inside the duct 22, such that the fluid inlets 22a are spaced apart from each other.

In addition, the capsule body 10 has a fluid inflow space 10a defined therein, which is divided by a partition plate 14 and into which the fluid discharged to the fan units 20 is introduced.

In addition, the capsule body 10 has a body inlet 10b through which the fluid is introduced into the fluid inflow space 10a. In an example, a plurality of the body inlets 10b is provided in the outer surface of the capsule body 10, such that the body inlets 10b are spaced apart from each other.

In addition, the capsule endoscope of the invention further includes fluid passage duct members 80, which are disposed inside the fluid inflow space 10a, and inside each of which a corresponding fan unit 20 and a corresponding fan position-changing device 30 are mounted. The fluid passage duct member 80 has a duct inlet 81 through which the fluid is introduced into the fluid passage duct member 80. In an example, a plurality of the duct inlets 81 is provided in the outer surface of the duct member 80 such that the duct inlets 81 are spaced apart from each other.

The fluid inflow space 10a of the capsule body 10 is filled with the fluid, which is introduced thereinto through the body inlets 10b.

When the fan unit operates 20, that is, the fan 21 rotates, the fluid is introduced into the fluid inflow space 10a through the body inlets 10b, and is then discharged to the outlet side of the duct 22 through the duct inlets 81 and the fluid inlets 22a.

The partition plate 14 provides a complete seal to the fluid inflow space 10a in order to prevent the fluid introduced into the fluid inflow space 10a from entering the camera 11, the wireless transceiver 12 and the battery 13, which are disposed inside the capsule body 10, which would otherwise malfunction because of the fluid that is introduced thereto.

The fan units 20 include a first fan unit 20a, which is mounted in the capsule body 10 and discharges the fluid out of the capsule body 10, and a second fan unit 20b, which is mounted in the capsule body at a position that is opposite the first fan unit 20a. The second fan unit 20b discharges the fluid in a direction different from that of the first fan unit 20a.

Each of the first fan unit 20a and the second fan unit 20b has a fan motor connected to a corresponding fan 21 in order to rotate the fan 21 due to the operation of the motor.

The direction in which the fan unit 20 is changed by the fan position-changing devices 30.

The respective fan position-changing devices 30 are connected to the respective fan units 20, that is, to the first fan unit 20a and to the second fan unit 20b, such that the direction in which the fans 21 operate to discharge the fluid is changed in response to the operation of the fan position-changing devices 30.

Figure 2:
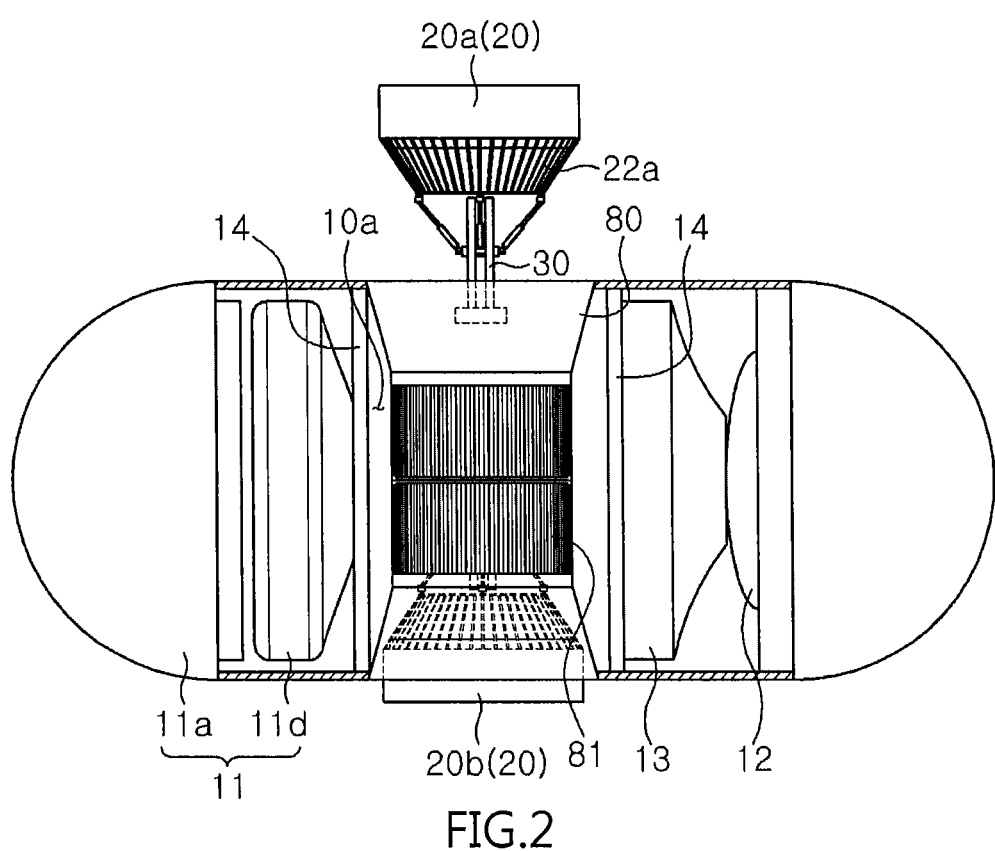
FIG. 2 is a cross-sectional view showing a capsule endoscope according to the invention.

For reference, FIG. 2 is a view that separately shows the first and second fan units 20a and 20b and the fan position-changing devices 30, which change the direction in which the fluid is discharged by the fan units 20a and 20b.

The fan position-changing devices 30 change the position at which the fan units 20a and 20b discharge the fluid. In an example, the fan position-changing devices 30 are mounted inside the fluid inflow space 10a of the capsule body 10, and are disposed in a vertical direction in the capsule body 10 facing oppositely in order to cause the first and second fan units 20a and 20b to discharge the fluid upward and downward.

Each fan position-changing devices 30 includes a fan-fixing section to which the fan unit 20 is fixed, fan supports 50 to which the fan-fixing section 40 is connected such that an angle is freely adjustable, and a plurality of angle adjustment sections 60, which is disposed below the fan-fixing section 40 such that the angle adjustment sections 60 are spaced apart from each other. The angle adjustment sections 60 serve to change the angle of the fan-fixing section 40.

In addition, each of the fan position-changing devices 30 also includes a wireless controller, which controls the angle adjustment sections 60 from the outside of the capsule body 10. The wireless controller transmits the operation control signal of the angle adjustment sections 60 to the wireless transceiver 12, which receives the operation control signal and transmits the operation control signal to the angle adjustment sections 60.

The fan-fixing section 40 includes a fixing panel on which a corresponding one of the fan units 20 is seated. The fixing panel has the shape of a circle that corresponds to that of the fan unit 20.

Figure 4:
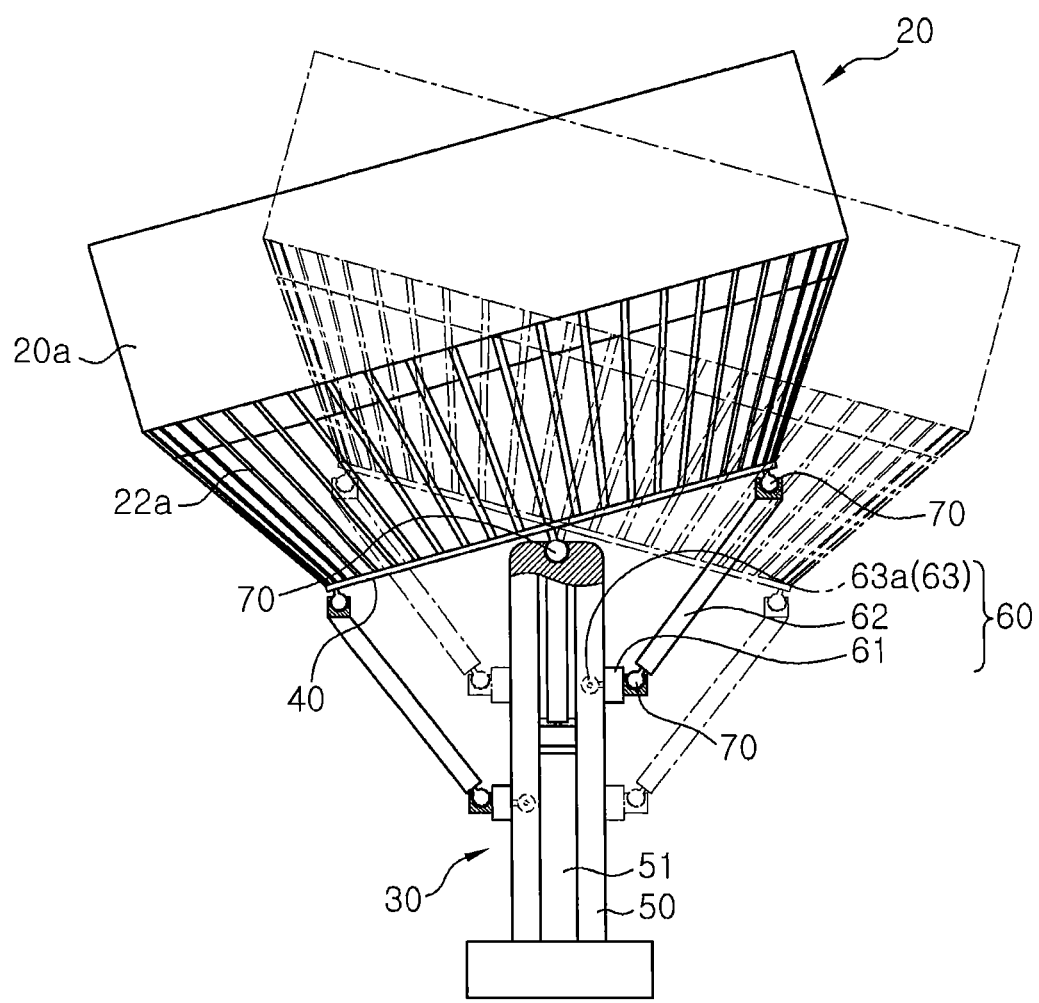
FIG. 4 is a view showing an embodiment of a fan position-changing device using a movable member according to the invention.

Referring to FIG. 4, the fan-fixing section 40 and the fan supports 50 are connected to each other by ball connectors 70 such that the angle of the fan-fixing section 40 can be adjusted in any direction.

The fan supports 50 are connected to the fan-fixing section 40 at a position corresponding to the central portion of the fan unit 20, which is seated and mounted on the fan-fixing section 40.

Each of the angle adjustment sections 60 includes a movable member 61, which is provided on a corresponding fan support 50 such that is movable in the longitudinal direction of the fan support 50, a connecting link member 62, which is connected to the movable member 61 and the fan-fixing section 40, and an actuator 63, which actuates the movable member 61 so that it linearly reciprocates.

The actuator 63 includes a wheel 63a and a motor (not shown), which rotates the wheel 63.

It should be understood that the actuator 63 can be modified into any structure as long as it causes the movable member 61 to linearly reciprocate.

The fan support 50 is provided with a guide rail 51 to which the movable member 61 is movably coupled. The movable member 61 linearly reciprocates along the guide rail 51, in the longitudinal direction of the fan support 50.

In an example, four angle adjustment sections 60 are disposed on the fan-fixing section 40, at intervals of 90° about the center of the fan unit 20.

Both ends of the connecting link member 62 are connected to the movable member 61 and to the fan fixing section 40 by ball connectors 70 such that the angle can be adjusted in any direction.

The four angle adjustment sections 60 are arranged at intervals of 90° as described above, thereby forming two pairs, which are disposed on both sides of the center of the fan units 20 such that they face each other.

A description will be given below of an example in which the angle of the fan units 20 is adjusted due to the operation of the angle adjustment sections 60.

When the actuator 63 of one angle adjustment section 60 of one pair of the angle adjustment sections 60 operates so that the movable member 61 moves toward the corresponding fan unit 20, the other actuator 63 in the opposite position moves the movable member 61 in the opposite direction, thereby adjusting the direction, i.e. angle, in which the fan unit 20 discharges fluid.

In addition, when the actuator 63 of one angle adjustment section 60 of one pair of the angle adjustment sections 60 operates to move the movable member 61 away from the fan unit 20, the opposite actuator 63 moves the movable member 61 in the opposite direction, thereby adjusting the direction, i.e. angle, in which the fan unit 20 discharges the fluid.

The other pair of the angle adjustment sections 60 operates according to the same principle as specified above, thereby adjusting the direction, i.e. angle, in which the fan unit 20 discharges the fluid.

Figure 5:
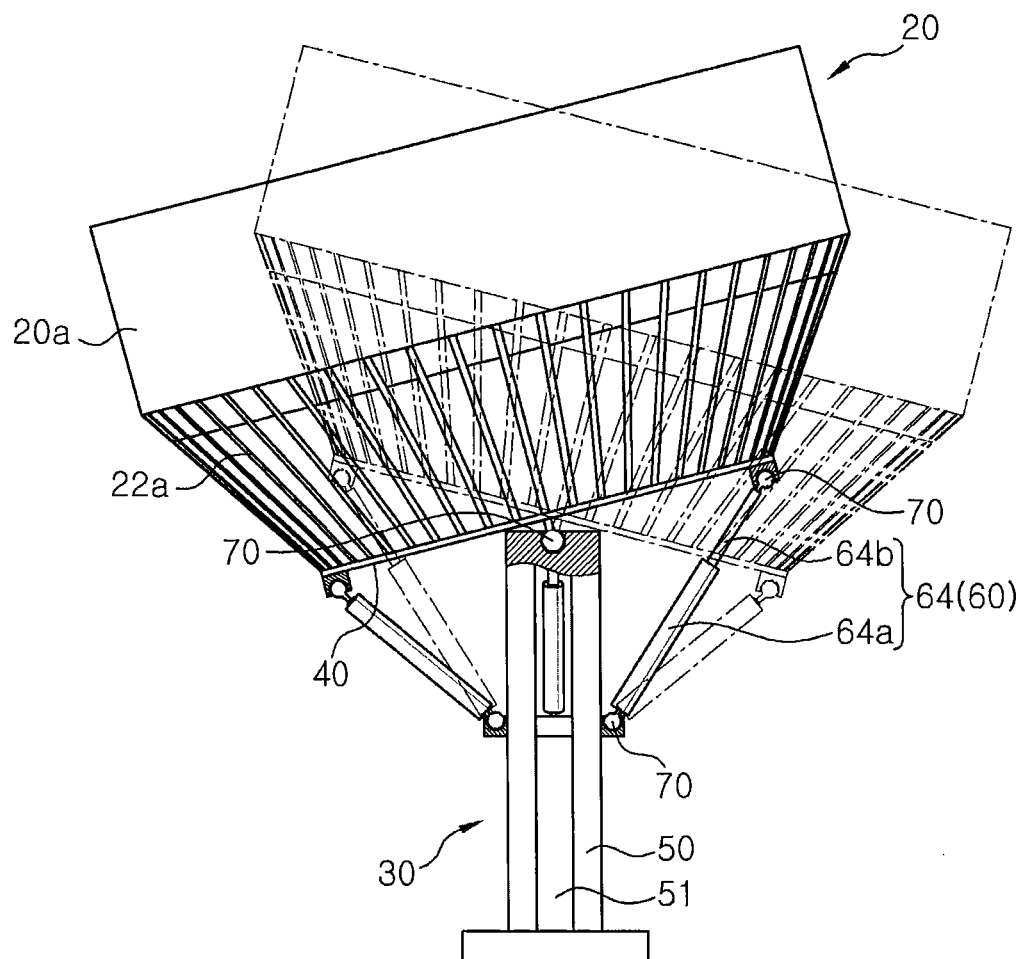
FIG. 5 is a view showing an embodiment of a fan position-changing device using a actuation link member according to the invention.
Figure 6:
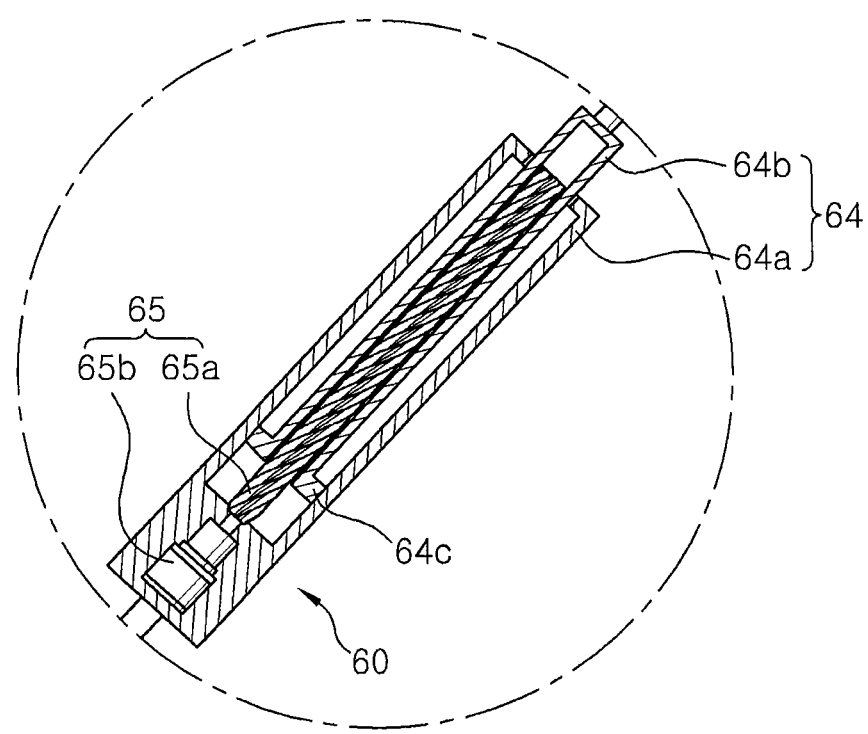
FIG. 6 is a cross-sectional view showing an operating link member according to the invention.

As shown in FIG. 5 and FIG. 6, each of the angle adjustment sections 60 includes an actuation link member 64, which is connected to the fan-fixing section 40 and the corresponding fan support 50 and is adjustable in length, and a link-moving section 65, which adjusts the length of the actuation link member 64.

In an example, the four angle adjustment sections 60 are disposed on the fan-fixing section 40, at intervals of 90° about the center of the fan unit 20.

Both ends of the actuation link member 64 are connected to the fan fixing section 40 and to the movable member 61 via the ball connectors 70 such that the angle can be adjusted in any direction.

The four angle adjustment sections 60 are arranged at 90° intervals as described above, thereby forming two pairs, which are disposed on both sides of the center of the fan units 20 and face each other.

The actuation link member 64 includes a fixing link 64a, which is connected to one of the fan-fixing section 40 and the fan support 50, and a movable link 64b, which is movably coupled to the fixing link 64a and is connected to the other one of the fan-fixing section 40 and the fan support 50.

The link-moving section 65 includes a movable screw 65a, which is disposed in the longitudinal direction of the fixing link 64a and to which the movable link 64b is screw-coupled, and a screw-rotating motor 65b, which rotates the movable screw 65a.

In an example, the movable link 64b is movably coupled to the inside of the fixing link 64a.

A movement guide protrusion 64c protrudes from the outer circumference of the movable link 64b. The movement guide protrusion 64c is held inside the fixing link 64a so that the movable link 64b is not rotated by the rotation of the screw.

Following the direction in which the movable screw 65a operated by the screw-rotating motor 65b rotates, the movable link 64b linearly reciprocates in the longitudinal direction of the fixing link 64a, thereby adjusting the length of the actuation link member 64.

A description will be given below of an example in which the angle of the fan unit 20 is adjusted in response to the operation of the angle adjustment sections 60.

When the link-moving section 65 of one angle adjustment section 60 of one pair of the angle adjustment sections 60 is operated to increase the length of the actuation link member 64, the opposite link-moving section 65 decreases the length of the actuation link member 64, thereby adjusting the direction in which the fan unit 20 discharges the fluid, i.e. the angle of the fan unit 20.

In addition, when the link-moving section 65 of one angle adjustment section 60 of the other pair of the angle adjustment sections 60 is operated to decrease the length of the actuation link member 64, the opposite link-moving section 65 increases the length of the actuation link member 64, thereby adjusting the direction in which the fan unit 20 discharges the fluid, i.e. the angle of the fan unit 20.

The other pair of the angle adjustment sections 60 operates according to the same operating principle, thereby adjusting the direction in which the fan unit 20 discharges the fluid, i.e. the angle of the fan unit 20.

As described above, according to the invention, the angles of the first fan unit 20a and the second fan unit 20b, which are disposed so as to face each other in the capsule body 10, are adjusted in response to the operation of the angle adjustment sections 60, thereby changing the direction in which the fluid is discharged.

Figure 7:
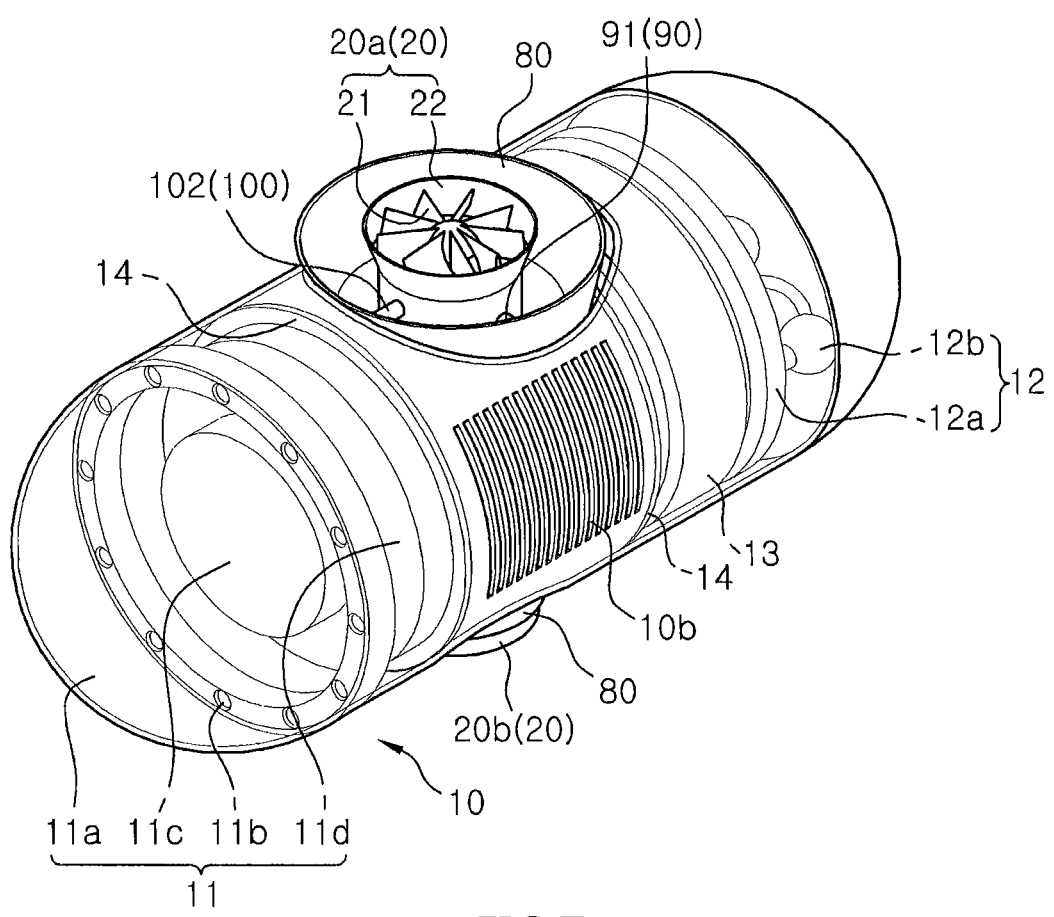
FIG. 7 is a perspective view showing another embodiment of the capsule endoscope according to the invention.
Figure 8:
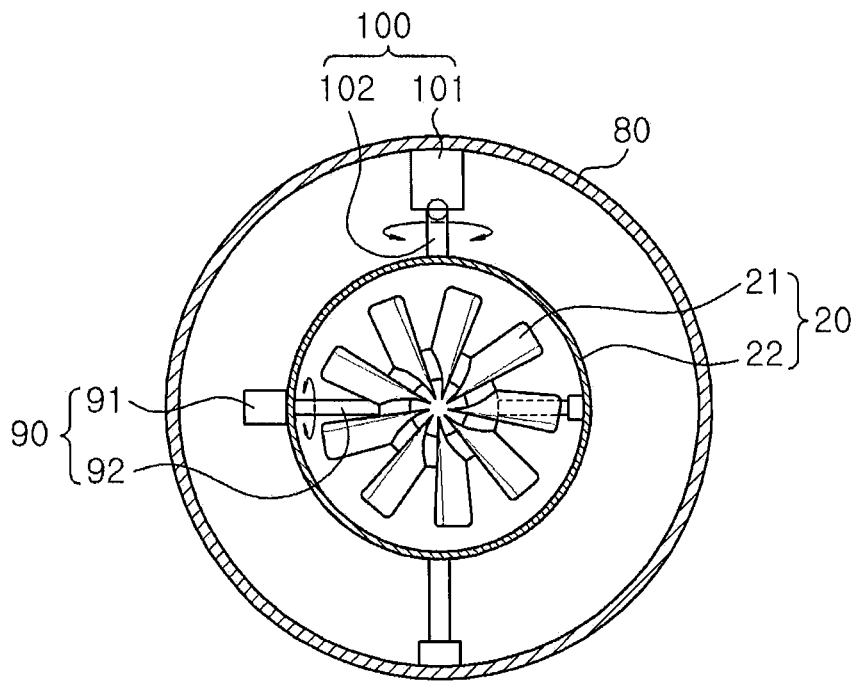
FIG. 8 is a top view showing another embodiment of a fan position-changing device according to the invention.
Figure 9:
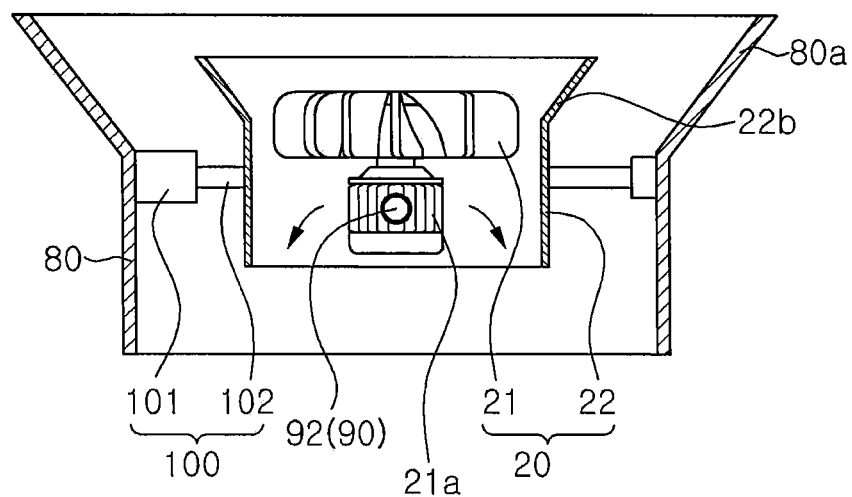
FIGS. 9 and 10 are cross-sectional view showing another embodiment of fan position-changing device according to the invention.

Referring to FIG. 7 to FIG. 9, the fan position-changing device 30 includes a duct-rotating section 100, which is provided in the duct 22, and is connected to a fan-rotating section 90 and the duct 22. The fan-rotating section 90 changes the blowing direction of the fan 21 by rotating the fan 21, which is connected to and is rotated by the fan motor 21a. Therefore, the direction of rotation of the duct-rotating section 100 is different from the direction of rotation of the fan 21.

The fan-rotating section 90 includes a first motor 91, which is mounted on the duct 22 and generates rotational force, and a first rotary shaft 92, which rotates using the rotational force delivered from the first motor 91. The first rotary shaft 92 is connected to the fan 21 so as to rotate the fan 21.

The first rotary shaft 92 is connected to the fan motor 21a, which rotates the fan 21, thereby allowing the fan 21 to be rotated by the fan motor 21a. The first rotary shaft 92 may be connected to an outer portion of the casing of the fan motor 21a, and be connected to a separate fixing bracket (not shown) to which the fan motor 21 is fixed.

In addition, the duct-rotating section 100 includes a second motor 101, which is mounted inside the capsule body and generates rotational force, and a second rotary shaft 102, which rotates using the rotational force delivered from the first motor 101. The second rotary shaft 102 is connected to the fan 22 so as to rotate the fan 22.

In an example, the duct-rotating section 100 is mounted inside the fluid passage duct member 80. The first rotary shaft 92 and the second rotary shaft 102 are disposed in opposite directions about the center of rotation of the fan. In an example, the directions of their shafts are disposed so as to be perpendicular to each other on the plane of the fan.

The fan position-changing device 30 further includes a wireless controller, which controls the fan-rotating section 90 and the duct-rotating section 100 from outside of the capsule body 10. The wireless controller delivers the operation control signal for the fan-rotating section 90 and the duct-rotating section 100 to the wireless transceiver 12, which after receiving the operation control signal, delivers it to the fan-rotating section 90 and the duct-rotating section 100.

Referring to FIG. 9, the fan-rotating section 90 allows the fan 21 to be rotated by the fan motor 21a about the first rotary shaft 92, thereby changing the direction in which the fan 21 discharges the fluid.

Figure 10:
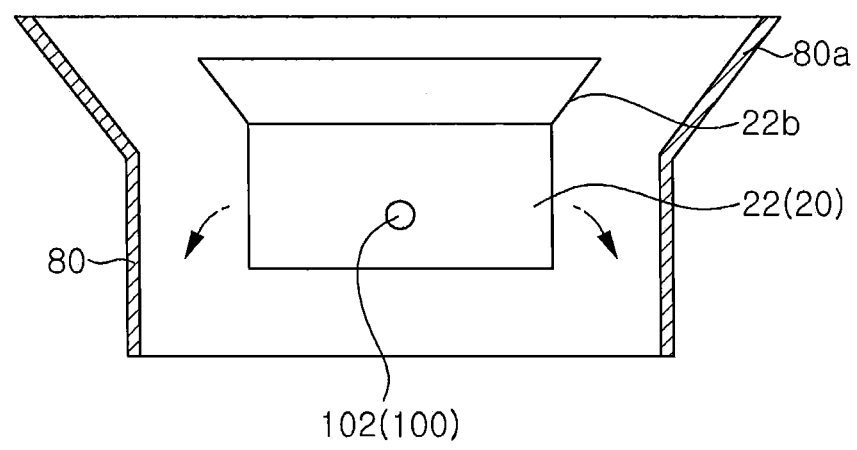

In addition, referring to FIG. 10, the duct-rotating section 100 rotates the duct 22 about the second rotary shaft 102, thereby changing the direction in which the fan 21 discharges the fluid.

In this way, the fan position-changing device 30 rotates the fan about the rotary shafts, which are perpendicular to each other on the plane of the fan 21, thereby changing the direction in which the fan 21 discharges the fluid.

It is preferred that the duct 22 have a first discharge guide corn 22b which gradually increases in diameter in the direction in which the fluid is discharged. This configuration provides a space in which to efficiently perform the discharging in response to the rotation of the fan 21.

In addition, it is preferred that the fluid passage duct member 80 have a second discharge guide corn 80a which has a diameter that gradually increases in the direction in which the fluid is discharged. This configuration provides a space to efficiently perform the discharging in response to the rotation of the duct 22.

The capsule body 10 can change the position with six degrees of freedom. The capsule endoscope of the invention can freely change the position of the capsule body 10 inside the internal organ by changing the discharge directions of the first and second fan sections 20a and 20b, which face each other, in response to the operation of the fan position-changing devices 30.

In addition, it is possible to concentrically take photographs of a specific region that is intended to be photographed.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A capsule endoscope comprising:
   a capsule body comprising a camera capable of taking an image of an inside of an internal organ and a wireless transceiver, which communicates with an outside in order to control a movement of the capsule endoscope;
   a fan unit, which is mounted on the capsule body and is rotated by a motor, thereby discharging a fluid out of the capsule body; and
   a fan position-changing device, which changes a direction in which the fan unit discharges the fluid;
   wherein the fan unit comprises a fan, which is rotated by the motor, and a duct, in which the fan is disposed;
   wherein the duct has a fluid inlet through which the fluid is introduced into the duct when the fan operates;
   wherein the capsule body has a fluid inflow space formed therein, wherein the fluid inflow space is divided by a partition plate, and the fluid to be discharged by the fan unit is introduced into the fluid inflow space; and
   a fluid passage duct member disposed in the fluid inflow space, wherein the fan unit and the fan position-changing device are mounted inside the fluid passage duct member, and wherein the fluid passage duct member has a duct inlet through which the fluid is introduced.

2. The capsule endoscope of claim 1, wherein the fan unit includes:
   a first fan unit, which is mounted on the capsule body, and discharges the fluid out of the capsule body; and
   a second fan unit, which is mounted opposite the first fan unit in the capsule body, and discharges the fluid in a direction different from that of the first fan unit.

3. The capsule endoscope of claim 2,
   wherein the first fan unit and the second fan unit are disposed in a vertical direction of the capsule body facing oppositely in order to discharge the fluid upward and downward with respect to the capsule body.

4. The capsule endoscope of claim 1, wherein the fan position-changing device comprises:
   a fan-fixing section to which the fan unit is fixed;
   a fan support to which the fan-fixing section is connected such that an angle thereof is freely adjustable; and
   a plurality of angle adjustment sections, which are disposed below the fan-fixing section and are spaced apart from each other, the angle adjustment sections changing an angle of the fan-fixing section.

5. The capsule endoscope of claim 4, wherein the fan-fixing section and the fan support are connected to each other by a ball connector.

6. The capsule endoscope of claim 4, wherein each of the angle adjustment sections comprises:
   a first movable member, which is provided on the fan support such that the first movable member is movable upward and downward;
   a connecting link member, which is connected to the first movable member and the fan-fixing section; and
   an actuator, which operates to linearly move the first movable member.

7. The capsule endoscope of claim 6, wherein both ends of the connecting link member are connected to the first movable member and to the fan-fixing section by ball connectors, respectively.

8. The capsule endoscope of claim 4, wherein each of the angle adjustment sections comprises:
   an actuation link member, which is connected to the fan-fixing section and the fan support and which has an adjustable length; and
   a link-moving section, which adjusts the length of the actuation link member.

9. The capsule endoscope of claim 8, wherein both ends of the actuation link member are connected to the fan-fixing section and the fan support by ball connectors, respectively.

10. The capsule endoscope of claim 8, wherein the actuation link member comprises:
    a fixing link, which is connected to one of the fan-fixing section and the fan support; and
    a movable link, which is movably coupled to the fixing link, and is connected to the other one of the fan-fixing section and the fan support.

11. The capsule endoscope of claim 10, wherein the link-moving section comprises:
    a movable screw, which is disposed in a longitudinal direction of the fixing link, and to which the movable link is screw-coupled; and
    a motor, which rotates the movable screw.

12. The capsule endoscope of claim 11, wherein
    the movable link is movably connected to an inside of the fixing link, and
    a movement guide protrusion extends from an outer circumference of the movable link, the movement guide protrusion being held inside the fixing link in order to prevent the movable link from rotating along with the screw when the screw rotates.

13. The capsule endoscope of claim 4, wherein the angle adjustment sections are disposed below the fan-fixing section, at intervals of 90° about a central portion of the fan unit.

14. The capsule endoscope of claim 1, wherein
    the fan unit comprises:
    a fan, which is rotated by the motor; and
    a duct inside which the fan is disposed, and
    the fan position-changing device comprises:
    a fan-rotating section, which is provided in the duct, and changes the direction in which the fan discharges the fluid by rotating the fan; and
    a duct-rotating section, which is connected to the duct, and rotates the duct in a direction different from a direction in which the fan rotates.

15. The capsule endoscope of claim 14, wherein
    the fan-rotating section comprises:
    a first motor, which is mounted on the duct, and generates rotational force; and a first rotary shaft, which rotates by receiving the rotational force from the first motor, and is connected to the fan such that the fan rotates, and the duct-rotating section comprises:

a second motor, which is mounted in the capsule body, and generates rotational force; and a second rotary shaft, which rotates by receiving the rotational force from the second motor, and is connected to the duct such that the duct rotates.

16. The capsule endoscope of claim 15, wherein the first rotary shaft and the second rotary shaft are disposed such that the first and second rotary shafts are perpendicular to each other on a plane.

17. A capsule endoscope comprising:

a capsule body comprising a camera capable of taking an image of an inside of an internal organ and a wireless transceiver, which communicates with an outside in order to control a movement of the capsule endoscope;

a fan unit, which is mounted on the capsule body and is rotated by a motor, thereby discharging a fluid out of the capsule body;

a fan position-changing device, which changes a direction in which the fan unit discharges the fluid; and wherein the fan position-changing device comprises:

a fan-fixing section to which the fan unit is fixed;

a fan support to which the fan-fixing section is connected such that an angle thereof is freely adjustable; and a plurality of angle adjustment sections, which are disposed below the fan-fixing section and are spaced apart from each other, the angle adjustment sections changing an angle of the fan-fixing section; and wherein each of the angle adjustment sections comprises:

an actuation link member, which is connected to the fan-fixing section and the fan support and which has an adjustable length; and a link-moving section, which adjusts the length of the actuation link member.

18. The capsule endoscope of claim 17, wherein both ends of the actuation link member are connected to the fan-fixing section and the fan support by ball connectors, respectively.

19. The capsule endoscope of claim 17, wherein the actuation link member comprises:

a fixing link, which is connected to one of the fan-fixing section and the fan support; and a movable link, which is movably coupled to the fixing link, and is connected to the other one of the fan-fixing section and the fan support.

20. A capsule endoscope comprising:

a capsule body comprising a camera capable of taking an image of an inside of an internal organ and a wireless transceiver, which communicates with an outside in order to control a movement of the capsule endoscope;

a fan unit, which is mounted on the capsule body and is rotated by a motor, thereby discharging a fluid out of the capsule body;

a fan position-changing device, which changes a direction in which the fan unit discharges the fluid; and wherein the fan unit comprises:

a fan, which is rotated by the motor; and a duct inside which the fan is disposed, and wherein the fan position-changing device comprises:

a fan-rotating section, which is provided in the duct, and changes the direction in which the fan discharges the fluid by rotating the fan; and a duct-rotating section, which is connected to the duct, and rotates the duct in a direction different from a direction in which the fan rotates.

* * * * *